United States Patent [19]

Brunelli et al.

[11] Patent Number: 4,623,288
[45] Date of Patent: Nov. 18, 1986

[54] APPARATUS FOR PRODUCING TISSUE COMPENSATING FILTER FOR USE IN RADIATION

[75] Inventors: Richard J. Brunelli, San Jose; Scott J. Mestman, Sunnyvale, both of Calif.

[73] Assignee: Varian Associates, Inc., Palo Alto, Calif.

[21] Appl. No.: 637,349

[22] Filed: Aug. 6, 1984

Related U.S. Application Data

[63] Continuation of Ser. No. 432,605, Oct. 4, 1982, abandoned.

[51] Int. Cl.⁴ .................. B23C 1/16; B29C 33/38
[52] U.S. Cl. .................... 409/84; 33/23.09;
  128/659; 264/222; 409/90; 409/93; 409/103
[58] Field of Search .................. 264/222, DIG. 30;
  409/84, 89, 90, 92, 93, 103; 33/23.09, 24.1, 24.2;
  128/1.1, 653, 659

[56] References Cited

U.S. PATENT DOCUMENTS

| | | | |
|---|---|---|---|
| 663,563 | 12/1900 | Eaton | 33/24 B |
| 1,059,893 | 4/1913 | Milde | 33/24 B |
| 1,271,461 | 7/1918 | Hanna | 33/23 M |
| 2,018,435 | 10/1935 | Bickel | 409/84 |
| 3,321,832 | 5/1967 | Weisberg | 409/84 |
| 3,755,672 | 8/1973 | Edholm et al. | 378/159 |
| 3,975,983 | 8/1976 | Stockman | 409/84 |

OTHER PUBLICATIONS

Fletcher, Gilbert H., "Textbook of Radiotherapy", 3rd edition, Lea & Febiger, 1980, pp. 11-24.
"Electronics and Nucleonics Dictionary", 3rd edition, published by McGraw-Hill Book Company, 1966, p. 337.
Johns and Cunningham, The Physics of Radiology, Thomas Books, pp. 404-407 (1974).
Cunningham et al, "A Semiautomatic Cutter for Compensating Filters", International Journal Oncology-Biology-Physics, 1976, vol. 1, pp. 355-360.
Kahn, Moore and Burns, "An Apparatus for the Construction of Irregular Surface Compensators for Use in Radiotherapy", Radiology, vol. 90, No. 3, pp. 593-594, Mar. 1968.

Primary Examiner—James Lowe
Attorney, Agent, or Firm—Stanley Z. Cole

[57] ABSTRACT

Apparatus for fabricating a compensating filter for use in radiation therapy includes a stylus for tracing the profile of a surface portion of a patient and a cutter for cutting a form. The stylus and cutter are positioned on first and second guides which are connected by a tie bar. A plurality of linkages translate movement of the stylus along its guide to the cutter along its guide. A mold is cut in the form which is filled with compensating material for forming the filter. The ratio of movement of the stylus to the cutter is established by the linkages in accordance with the ratio of radiation absorption of the compensating material to the radiation absorption of human tissue.

14 Claims, 7 Drawing Figures

APPARATUS FOR PRODUCING TISSUE COMPENSATING FILTER FOR USE IN RADIATION

This application is a continuation of application Ser. No. 432,605, filed Oct. 4, 1982, now abandoned.

This invention relates generally to radiation therapy systems, and more particularly the invention relates to a method and means for producing a tissue compensating filter for use in radiation therapy.

Radiation therapy in treating tumors in a patient requires that uniform dosage of radiation be delivered in limited areas and at the tumor depth. However, it is known that radiation beams incident on irregular surfaces produce skewing of isodose curves. For example, in treating tumors in the chest, neck, and head areas radiation beams necessarily impinge on irregular skin surfaces which can result in skewed isodosage. See for example Johns and Cunningham, *The Physics of Radiology*, Thomas Books 1974, pgs. 404–407.

The use of a bolus abutting the skin or a compensating filter positioned away from the skin, in the radiation beam path, have been proposed for reshaping the isodose curves for uniform treatment of a tumor within a patient's body. The compensating filter is preferable to the bolus for treating tumors well below the skin surface since skin sparing is achieved. Johns and Cunningham suggest constructing compensating filters using thin sheets of lead each cut to a contour and glued together to form a composite laminar filter. Cunningham et al, "A Semiautomatic Cutter For Compensating Filters", *International Journal Radiation Oncology Biology-Physics*, 1976, Vol. 1, pgs. 355–360 teach the use of a milling machine for milling a filter based on a wax block which reproduces the shape of the patient's skin. Kahn et al "An Apparatus for the Construction of Irregular Surface Compensators For Use in Radiotherapy", *Radiology*, Vol. 90, No. 3, pgs. 593–594, March, 1968 disclose an apparatus having a plurality of adjustable rods for positioning on the skin of a patient for defining the filter contour.

All of these known methods of forming compensating filters are generally not very accurate and tend to be uncomfortable for the patient. The construction of a single compensator can be very time consuming and expensive. Further, the constructing of compensators requires considerable specialized skills with the apparatus.

The present invention is directed to an improved method and apparatus for producing a compensating filter.

Accordingly, an object of the invention is an improved method of producing a compensating filter which is easily implemented.

Another object of the invention is apparatus for use in fabricating a compensating filter which is accurate and flexible in use.

A further object of the invention is a more accurate and less expensive compensating filter for use in radiation therapy.

Briefly, in accordance with the invention a stylus is provided for tracing the contour of the patient's surface and a cutter is provided for cutting a form. The stylus and cutter are coupled whereby movement of the stylus causes movement of the cutter. A patient's contour is traced with the stylus, and a form is cut by the cutter thereby defining a cavity in the form corresponding to the traced portion of the patient. The cavity is then filled with a suitable material for molding the filter.

The apparatus includes a mechanical support and gantry to which are pivotally mounted a first guide and a second guide. The stylus and housing are cooperatively arranged to move along the first guide for following the contour of the patient, and the cutter and support housing are cooperatively arranged to move along the second guide for cutting material from the form. The stylus and housing are mechanically coupled to the cutter and housing whereby movement of the stylus and housing along the first guide moves the cutter and housing along the second guide. The mechanical coupling between the stylus and the cutter is preferably adjustable whereby movement of the stylus and cutter is in accordance with the ratio of radiation absorption of tissue to the radiation absorption of the compensator material.

BRIEF DESCRIPTION OF THE DRAWINGS

The invention and objects and features thereof will be more readily apparent from the following detailed description and appended claims when taken with the drawing, in which:

DESCRIPTION OF THE PREFERRED EMBODIMENTS

Figure 1:
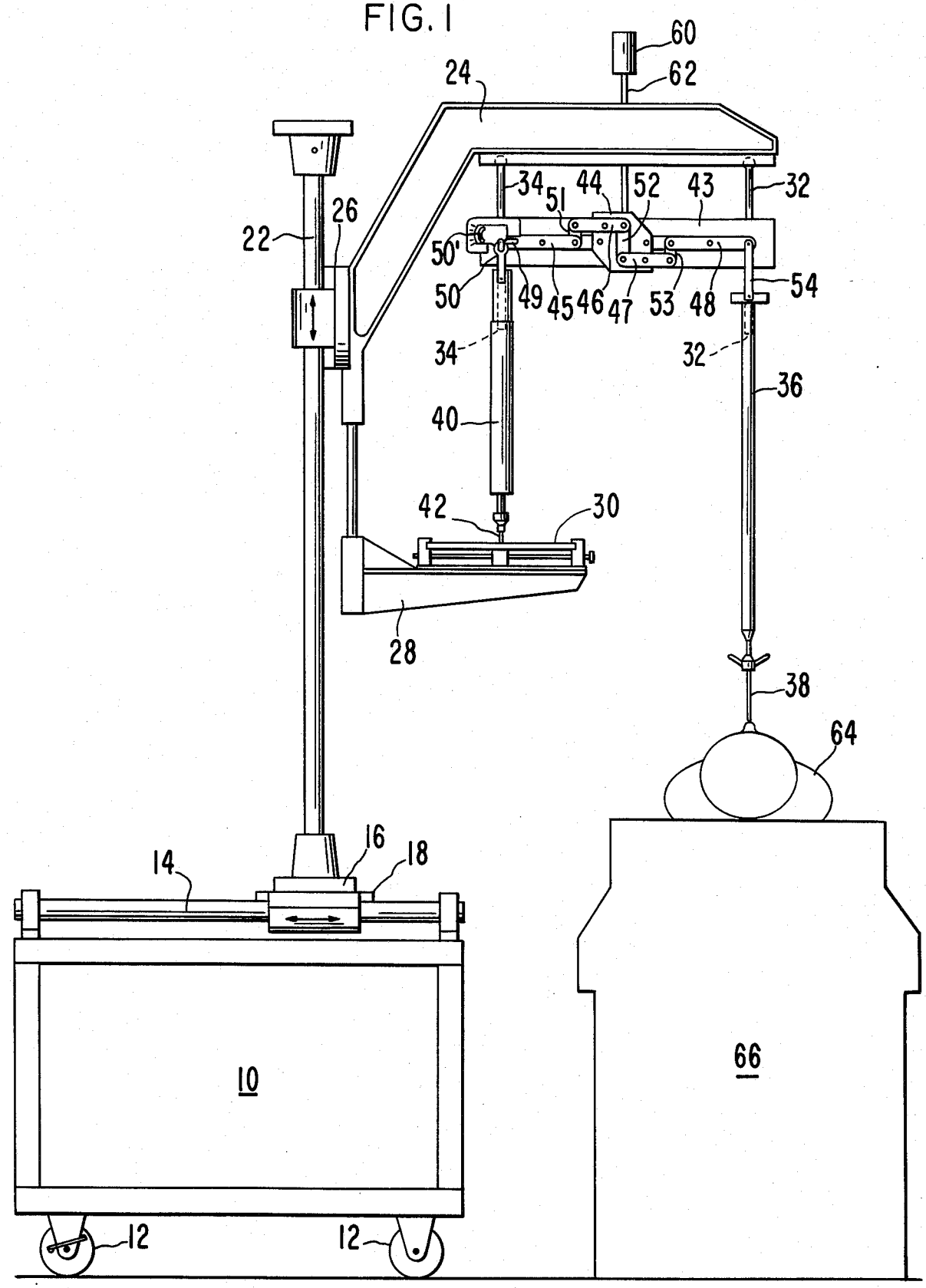
FIG. 1 is a front elevation view of apparatus in accordance with one embodiment of the invention.
Figure 2:
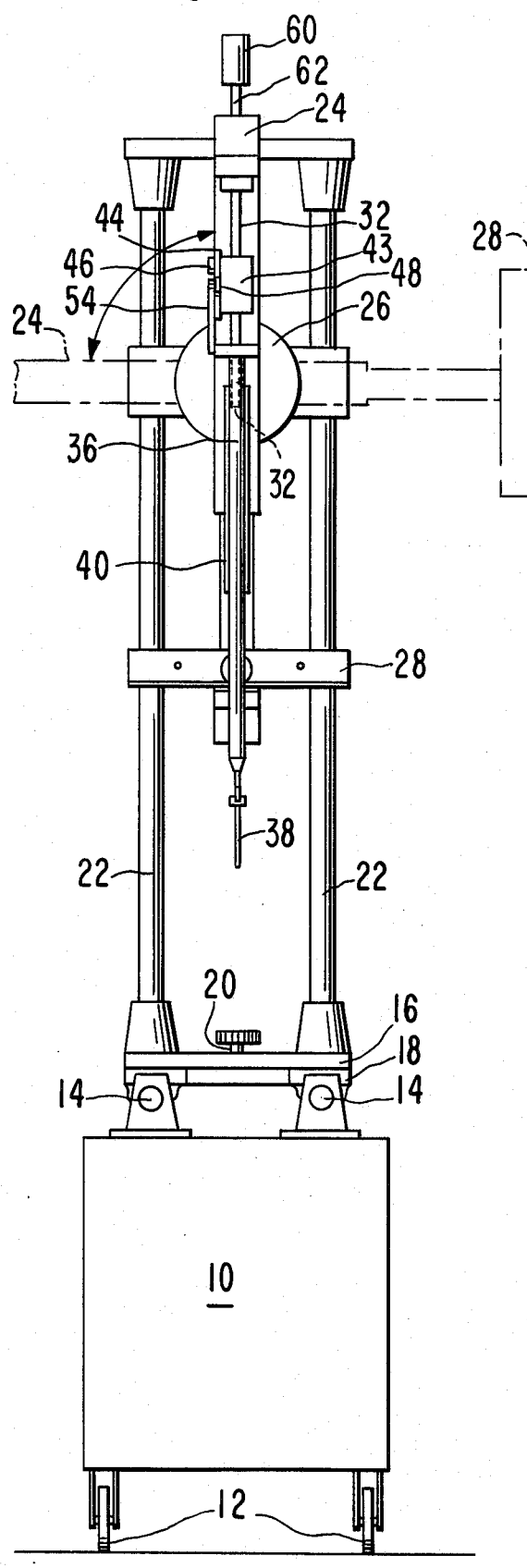
FIG. 2 is a side elevation of the apparatus of FIG. 1.

Referring now to the drawings, FIG. 1 and FIG. 2 are a front elevation view and a side elevation view, respectively, of apparatus in accordance with one embodiment of the invention. A mechanical support means includes a carriage 10 mounted on rollers 12 and having a pair of horizontal rods 14 mounted on the top surface. Slidably mounted on the horizontal rods 14 is a support platform including plates 16 and 18. Plate 16 is attached to plate 18 by means of a bolt 20, and plate 16 is rotatable on plate 18 upon loosening of bolt 20.

Mounted on plate 16 are a pair of vertical columns 22, and extending from the columns 22 is a gantry support beam 24 which is coupled to the vertical columns 22 by means of a coupler 26 which is slidably moveable on the vertical columns by motor means (not shown). Depending from the support beam 24 and coupler 26 is a platform 28 on which a form 30 is mounted.

Pivotally mounted to the support beam 24 are a first guide rod 32 and a second guide rod 34 so that the rods 32 and 34 can swing around their respective pivot points both front to back and side to side. Slidably mounted on the first guide rod 32 is a stylus housing 36 including a stylus 38 depending therefrom. Mounted on the second guide 34 is a cutter housing 40 and a cutter 42 depending therefrom. Preferably, the cutter 42 is a air powered dental drill.

Pivotally attached to guide rods 32, 34 is a tie bar 43 which couples rotation of guide rod 32 to guide rod 34. A plate 44 is attached to the tie bar 43. Pivotally attached to the tie bar 43 and plate 44 are linkages 45, 46, 47, and 48. One end of linkage 45 includes a slot 49 to which the drill housing 40 is adjustably pivotally attached by a linkage 50 to vary the ratio of travel. The pivot point of linkage 50 in slot 49 is established by rotating plate 50', which is adjustably pivotally attached to linkage bar 45, thereby sliding a pivot pin in the slot 49. The opposite end of linkage 45 is attached to linkage 46 by means of intermediate linkage 51. The opposite end of linkage 46 is attached to one end of linkage 47 by means of intermediate linkage 52. The opposite end of linkage 47 is attached to one end of linkage 48 by means of intermediate linkage 53, and the opposite end of linkage 48 is pivotally attached to the stylus housing 36 by means of linkage 54.

Mounted on the opposite side of the gantry support beam 24 is a counterweight 60 and support rod 62. Rod 62 passes through gantry 24 and is pivotally attached to the tie bar 44. The support beam 24 is rotatable on coupler 26 (as shown in dotted form in FIG. 2), and the counterweight 60 provides a counterbalance to the guides 32, 34, stylus housing 36, drill housing 40, the tie bar 44 and linkages attached thereto.

In operation, a patient 64 on table 66 is positioned beneath the stylus 38, and the form 30 is positioned beneath the cutter 42. As the stylus traces the contour of the portion of the patient to be irradiated, the cutter 42 is moved by the coupling mechanism and cuts the form 30 in a pattern corresponding to the contour of the patient. A shield (not shown) can be provided around the cutter 42 and form 30. Preferably, the form 30 is an easily machined material such as styrofoam, and the contour surface to be irradiated is readily defined therein. Assuming for illustration purposes that the facial portion of a patient is to be irradiated, an image of the face is cut in the form as illustrated in the perspective view of form 30 in FIG. 3. The distance from the pivot point of guide 32 on gantry 24 to the patient 64 is the same distance as the radiation source in the therapy apparatus to the patient. The distance of the form 30 on platform 28 from the pivot point of guide 34 on gantry 24 corresponds to the position of the compensating filter in the radiation beam during the radiation therapy, as will be described further hereinbelow with reference to FIG. 7. The ratio of vertical movement of the drill 42 with respect to the stylus 38 (and hence the depth of the cavity in the form 30 in FIG. 3) is determined by the ratio of radiation absorption of the filter material to the radiation absorption of human tissue. In one embodiment the filter material is Cerrobend which is a low melting alloy of lead, bismuth, and cadmium available from Cerrometal Products, Belafonte, Pa. The radiation absorption by Cerrobend is nominally 9.4 times the radiation absorption of human tissue. Accordingly, the drill cuts the styrofoam block to a radial depth equal to one over the reducing factor (1/9.4) and appropriately demagnifies the width of the divergent beam. However, since the attenuation coefficient of Cerrobend varies with energy, the apparatus allows for this variation with the adjustment shown in FIG. 1.

Figure 3:
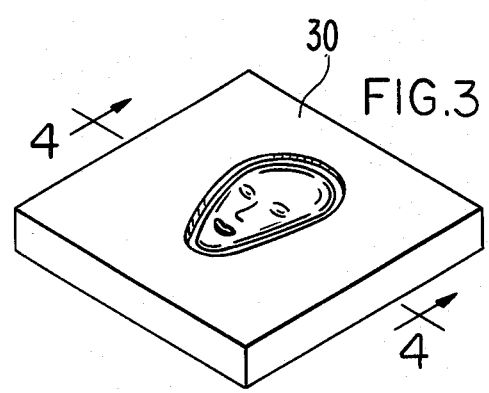
FIG. 3 is a perspective view of a form which has been cut using the apparatus of FIGS. 1 and 2.
Figure 4:
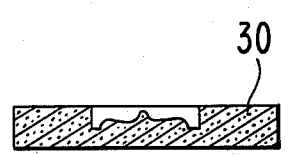
FIG. 4 and FIG. 5 are section views of the form of FIG. 3 taken along the line 4—4.
Figure 5:
Figure 6:
FIG. 6 is a section view of a compensating filter molded from the form of FIG. 3.
Figure 7:
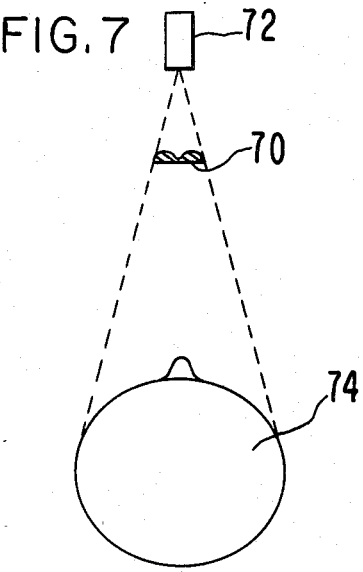
FIG. 7 is an illustrative view of radiation therapy apparatus including the compensating filter of FIG. 6.

FIG. 4 is a section view of the form 30 of FIG. 3 taken along the line 4—4 illustrating the machined contour corresponding to the facial features of the patient. In FIG. 5 the cavity is filled with Cerrobend material 70. The Cerroband material is heated to a liquid phase and poured into the machined form and then allowed to harden. After solidifying the finished compensating filter 70 is removed from the form 30 as shown in FIG. 6. FIG. 7 illustrates a radiation therapy system and shows the positioning of the compensating filter 70 in the path of the radiation beam from the radiation source 72 as directed on the head portion 74 of the patient. As described hereinabove, the position of the compensating filter in the radiation beam eliminates the skewing of isodose lines within the patient due to the irregular irradiated surface of the patient.

The method of forming a compensating filter using apparatus in accordance with the invention is quick and inexpensive, and the apparatus requires no specialized skill by the operator. The resulting compensating filter is very accurate. The sytrofoam form is disposable and the Cerrobend can be remelted and reused when the treatment schedule is fulfilled. The apparatus can be readily moved to facilitate use with the patient, and the method is very comfortable for the patient.

While the invention has been described with reference to a specific embodiment, the description is illustrative of the invention and is not to be construed as limiting the invention. Various modifications and applications may occur to those skilled in the art without departing from the true spirit and scope of the invention as defined by the appended claims.

What is claimed is:

1. Apparatus for making a cavity in a form, the cavity in the form being used to make a compensating radiation therapy filter of a predetermined material, the radiation therapy filter enabling a portion of a patient to be uniformly irradiated with isodose lines of radiation, the portion of the patient having irregular surfaces tending to produce skewing of isodose curves, the filter being placed at a predetermined position above and in alignment with the patient portion while treating the patient portion with a source of the radiation located a predetermined distance from the patient portion, said apparatus comprising:

a mechanical support means with a first pivotal point and a second pivotal point which are defined thereon and spaced from each other, a first guide pivotally mounted to said mechanical support means at said first pivotal point so as to be able to swing freely in multiple planes with respect to said mechanical support means around said first pivotal point, a second guide pivotally mounted to said mechanical support means at said second pivotal point so as to be able to swing freely in multiple planes with respect to said mechanical support means around said second pivotal point, a stylus and housing for the stylus mounted on the first guide as an extension thereof and cooperatively arranged to move along said first guide towards and away from said first pivotal point for three dimensionally following the contour of the patient portion, the distance of the stylus from the first pivot point being maintained so it is equal to the distance of the patient portion from the radiation source, a cutter and housing for the stylus mounted on the second guide as an extension thereof and cooperatively arranged to move along said second guide towards and away from said second pivotal point for three-dimensionally cutting material from the form, a first coupling means for coupling said stylus and housing for the stylus to said cutter and housing for the cutter so that movement of said stylus is geometrically similar to movement of said cutter and the position of the cutting tool from the second pivotal point is maintained so it is equal to the distance of the filter material from the radiation source, said first coupling means including a tie bar pivotally attached to said first guide and said second guide, and linkage means pivotally connected to said tie bar, said stylus and stylus housing and said cutter and cutter housing being attached to said linkage means at spaced-apart positions, and means for adjustably attaching said cutter housing to said linkage means for moving said cutter housing to different positions to provide different ratios of translation between said stylus and stylus housing and said cutter and cutter housing.

2. Apparatus as defined by claim 1 wherein said linkage means comprises four linkage bars pivotally attached to said tie bar and three intermediate linkages pivotally interconnecting said four linkage bars.

3. Apparatus as defined by claim 2 wherein one of said linkage bars includes a slot in which said cutter housing is adjustably pivotally mounted for adjusting the ratio of translation between said stylus and housing and said cutter and housing.

4. Apparatus as defined by claim 1 wherein said mechanical support means includes a plurality of vertical support columns, a support beam provided with said first and second pivotal points, second coupling means for slidably coupling said support beam to said vertical support columns, a plurality of horizontal support members, and third coupling means for slidably coupling said vertical support columns to said horizontal support members.

5. Apparatus as defined by claim 4 wherein said support beam is rotatable on said second coupling means and said vertical support columns are rotatable on said third coupling means.

6. Apparatus as defined by claim 4 and further including counter weight means and means for attaching said counter weight means to said support beam to counter balance the weight of said stylus and housing, said cutter and housing, said first guide, and said second guide.

7. Apparatus as defined by claim 5 and further including a carriage on which said horizontal support members are mounted.

8. Apparatus as defined by claim 4 and further including form support means, and means for attaching said form support means to said second coupling means in cooperative arrangement with said cutter.

9. Apparatus as defined by claim 8 and further including a table for supporting a patient in cooperative arrangement with said stylus.

10. Apparatus as defined by claim 1 wherein said first coupling means is so adapted that the motion of said stylus and stylus housing along said first guide is always parallel to the corresponding motion of said cutter and cutter housing along said second guide regardless of the instantaneous orientations of said guides with respect to said mechanical support means.

11. Apparatus as defined by claim 10 wherein said first coupling means is further so adapted that the distance by which said stylus and stylus housing are moved along said first guide and the distance by which said cutter and cutter housing are correspondingly moved along said second guide are at a pre-fixed ratio.

12. A method of making a cavity in a form, the cavity in the form being used to make a radiation therapy filter of a predetermined material, the radiation therapy filter enabling a portion of a patient to be uniformly irradiated with isodose lines of radiation, the portion of the patient having irregular surfaces tending to produce skewing of isodose curves, the filter being placed at a predetermined position above and in alignment with the patient portion while treating the patient portion with a source of the radiation located a predetermined distance from the patient portion, the method being performed with an apparatus including a stylus coupled to a cutting tool by an adjustable pantograph type linkage, the stylus being at one end of a first variable length rod having a second end mounted to pivot about a first pivot point, the cutting tool being at one end of a second variable length rod having a second end mounted to pivot about a second pivot point, the first and second pivot points being in the same horizontal plane, the linkage being constructed so that the ratio of movement of the stylus to the cutting tool is adjustable, the method comprising the steps of:

setting the linkage so the ratio of movement of the cutter to the movement of the stylus is equal to the ratio of the filter material radiation absorbtion to human tissue absorbtion, maintaining the distance of the stylus from the first pivot point so it is equal to the distance of the patient portion from the radiation source, maintaining the position of the cutting tool from the second pivot point so it is equal to the distance of the filter material from the radiation source, with the linkage so set and the distances so maintained and the patient portion in the same position relative to the radiation source as during treatment and the form in the same position relative to the radiation source as the filter during treatment, tracing the stylus over the patient portion by changing the length of the first rod so the first rod length conforms with the distance between the first pivot point and all of the patient portions as the first rod is swung in multiple planes about the first pivot point to cause the length of the second rod to be proportional to the length of the first rod and the second rod to swing about the second pivot point in multiple planes to follow the swinging of the first rod about the first pivot point so that a replica of the tracing motion of the stylus is reproduced with said ratio by the cutter on the form, the cutter cutting the form to enable a mold to be made for a compensating filter that overcomes the tendency to produce skewing of the isodose curves by the patient portion having irregular surfaces.

13. The method as defined by claim 12 further comprising the steps of providing a mechanical support means, a first guide and a second guide respectively forming parts of the first and second arms, and mounting said first and second guides pivotally to said mechanical support means so as to be freely swingable with respect to said mechanical support means respectively around a first pivotal point and a second pivotal point which are spaced from each other and defined on said mechanical support means, said stylus and said cutter being adapted to move respectively along said first and second guides towards and away from said first and second pivotal points.

14. The method as defined by claim 13 wherein said stylus and said cutter are so coupled that said first and second guides remain parallel to each other regardless of the orientations thereof with respect to said mechanical support means.

* * * * *